United States Patent
Maloney et al.

(10) Patent No.: US 8,597,613 B2
(45) Date of Patent: Dec. 3, 2013

(54) RADIOLABELED LYMPHATIC STAINING AGENTS AND METHODS FOR MAKING

(75) Inventors: Thomas J. Maloney, Friendswood, TX (US); Arthur E. Camp, Jr., Richmond, TX (US); Jesse J. Hernandez, Alvin, TX (US)

(73) Assignee: Iso-Tex Diagnostics, Inc, Friendswood, TX (US)

( * ) Notice: Subject to any disclaimer, the term of this patent is extended or adjusted under 35 U.S.C. 154(b) by 2231 days.

(21) Appl. No.: 10/884,561

(22) Filed: Jul. 2, 2004

(65) Prior Publication Data

US 2006/0002850 A1    Jan. 5, 2006

(51) Int. Cl.
*A61K 51/00* (2006.01)
*A61M 36/14* (2006.01)

(52) U.S. Cl.
USPC .......................................... 424/1.11; 424/1.85

(58) Field of Classification Search
None
See application file for complete search history.

(56) References Cited

U.S. PATENT DOCUMENTS

| | | | | |
|---|---|---|---|---|
| 4,851,520 A | * | 7/1989 | Kassis et al. | 536/26.14 |
| 6,448,299 B1 | * | 9/2002 | Brown et al. | 521/26 |
| 6,458,336 B1 | | 10/2002 | El-Tamer et al. | |
| 2004/0082863 A1 | | 4/2004 | McGreevy et al. | |

OTHER PUBLICATIONS

Raffaelli et al. (J. Chrom. A 1999, 854, 57-67).*
Helfferich, F. 1962, Ion Exchange, chapter 5, p230 a. Conditioning and Storage, New York: McGraw-Hill Book Company, Inc.*
Virgolini et al. Arterioscler. Thromb. Vasc. Biol. 1992, 12, 849-861.*
Blower et al. (Nuclear Med. Comm. 1990, 11, 413-420).*
Ünak et al. (Applied Radiation and Isotopes 2001, 54, 749-752).*
Deliisky, T. et al, "Sentinal Nody Biopsy a new Approach . . ." Euro Sod for Med Onco 1998, Abst. No. 26.
Tsopelas, C. et al "Why Certain Dyes are useful . . ." J of Nuc. Med. vol. 43 No. 10 1377-1382 (2002).
Blower, PJ et al, "Radioiodinated methylene blue . . ." (Abst. only) Nucl Med Biol May 1997; 24(4):305-310.
Link, EM "Targeting melanoma with 211At/131I-methylene blue . . ." (Abst only) Hybridoma Feb. 1999; 18(1):77-82.
Link, EM etal "Uptake and therapeutic effectiveness of:125I- . . . methylene blue . . ." (Abst) Canc Res Aug. 1, 1989; 49(15):4332-7.
Link, EM etal Early detection of metathesis with radioiodinated methylene blue (Abst) Eur J Nucl Med Sep. 1998; 25(9) 1332-9.
Uranium Information Centre, LTD (Australia) Radioisotopes in Medicine, Nuclear Issues Briefing Paper 26 (May 2004).
El-Tamer, M et al "A New Agent, Blue and Radioactive . . ." (Abst) Annals of Surg. Oncol. 10:323-329 (2003).
Bostick, P et al "Comparison of Blue Dye and . . ." (Abst) Archives of Surgery vol. 134 No. 1, Jan. 1999.
Young, Matt "Indocyanine green and trypan blue dyes offer . . ." Eye World Nov. 2003 p. 96.
Raffaelli, A et al, "Investigation on the iodination reaction of methylene blue . . ." J of Chromotog. A 854 (1999) 57-67.

* cited by examiner

*Primary Examiner* — Michael G Hartley
*Assistant Examiner* — Melissa Perreira
(74) *Attorney, Agent, or Firm* — John R Casperson

(57) ABSTRACT

A radiolabeled lymphatic staining agent is mixed on site with a much larger amount, on a weight basis, of a non-radiolabeled lymphatic staining agent to form an injectable radiolabeled lymphatic staining agent suitable for surgical use in humans. Preferably, the radiolabel is I-125, because it has a 60-day half-life which enables it to be made off-site. The preferred radiolabeled lymphatic staining agent is iodinated methylene blue, because it can be mixed with a range of non-radioactive lymphatic staining agents, for example isosulfan blue, methylene blue, patent blue, and patent blue V, to provide the injected agent with sufficient radioactivity to enable machine detection. A method for making radioiodinated methylene blue is also disclosed.

8 Claims, No Drawings

RADIOLABELED LYMPHATIC STAINING AGENTS AND METHODS FOR MAKING

FIELD OF THE INVENTION

In one aspect, the invention relates to radiolabeled lymphatic staining agents which are useful for detection of the sentinel lymph node draining a tumor site. In another aspect, the invention relates to a method for making such a staining agent. In a further aspect, the invention relates to a method for providing radiolabeled staining agents for use in lymph node detection.

BACKGROUND OF THE INVENTION

One of the major techniques for determining the prognosis of cancer, particularly breast cancer, involves examining the lymph nodes of the axilla or armpit of the patient. It is well known that a major aspect in assessing the stage of the cancer revolves around whether the cancer has spread to the lymph nodes. It is therefore important to have an effective technique for identifying the spread of the cancer through the lymphatic system.

In the lymphatic system of the human body, lymphatic fluid flows from the breast through the lymph channels and is filtered through the lymph nodes. The first stop is the "first lymph node" or the "sentinel lymph node." If the cancer has spread to the lymph nodes, the sentinel lymph node should be positive (i.e., cancerous). If the first lymph node is negative, it can be assumed that the rest of the lymph nodes are negative. Therefore, it is crucial that this first lymph node or sentinel lymph node be accurately identified.

A known technique for identifying the sentinel lymph node(s) involves the use of two substances: a blue dye and a radioactive substance. The blue dye visually stains the sentinel node(s) and the radioactive substance enables the site of the sentinel node(s) to be remotely detected. The blue dye conventionally used for sentinel lymph node procedure is lymphazurine blue, although smaller amounts of methylene blue have also sometimes been used, and still further substances have been suggested. The radioactive substance is a sulfur colloid. These substances are injected separately in or near the tumor or tumor site and flow along the lymphatic system to the sentinel node draining that site. The node can then be located by using a diagnostic device to detect the emissions from the radioactive substance and then visually accessing the node based on staining from the dye.

In less than 10 years from the first reports utilizing this technique, literally hundreds of studies have appeared in the scientific literature validating the use of sentinel node biopsy as an accurate method to evaluate the risk of harboring metastatic disease in axillary nodes. Almost simultaneously, reports appeared in the literature documenting the success of sentinel node localization using lymphazurin blue dye with or without technetium 99 labeled sulfur colloid. However, following the publication of large studies from Louisville as well as Memorial Sloan-Kettering, documenting improved success at harvesting the sentinel node as well as comparable accuracy, the majority of breast surgeons prefer to use both dye and radiocolloid for their evaluation of sentinel nodes.

Recently several reports have appeared suggesting that sentinel node accuracy and yield could be duplicated with the use of methylene blue dye as opposed to the lymphazurin blue dye. This change in dye preference has also found its way into practice of many surgeons. Injection of small quantities (0.1-0.5 cc) of methylene blue has been used for years. These small quantities of methylene blue are injected into the breast following wire-localization procedures and are associated with no reported adverse events.

With the development of sentinel node biopsy came some unanticipated consequences for both surgeon and patient alike. Patients must undergo a separate procedure for injecting the radiocolloid prior to their cancer surgery. This part of the procedure is carried out either the afternoon prior to surgery or the morning of surgery, usually within a couple of hours of the surgical procedure. The injection of radiocolloid is unusually painful whether it is injected in small quantities intradermally or in larger quantities around the tumor. With the increasing demand for sentinel lymph node sampling surgeons have been forced to deal with major delays in their surgical schedules because of the necessity of an additional preoperative procedure that is at the direction of non-operating room personnel.

Other shortcomings of the known procedures include the fact that 99M Tc sulfur colloid has high-energy gamma emissions and a significant amount of activity (10 mCi) has to be initially injected to ensure adequate node uptake. Some of the activity must clear from the injection site before use of the hand held gamma probe in the axilla. Failure to allow clearance of the radiolabeled colloid "swamps" the gamma detector making identification of the sentinel node impossible or at least much more difficult.

Therefore, there is a need for a composition that enables an improved and simplified technique for the identification of the sentinel lymph node.

OBJECTS OF THE INVENTION

It is an object of this invention to provide compositions suitable for the detection of the sentinel node.

It is a further object of this invention to provide methods for making the compositions.

SUMMARY OF THE INVENTION

In one embodiment of the invention, there is provided a composition of matter selected from the group consisting of phenothiazin-5-ium-3,7-bis(dimethylamino)-iodide; 4-iodo-phenothiazin-5-ium-3,7-bis(dimethylamino)-chloride; 4-iodo-phenothiazin-5-ium-3,7-bis(dimethylamino)-iodide; 4,6-diiodo-phenothiazin-5-ium-3,7-bis(dimethylamino)-chloride; 4,6-diiodo-phenothiazin-5-ium-3,7-bis(dimethylamino)-iodide, 4,6-diiodo-phenothiazin-5-ium-3,7-bis(methylamino)-chloride and 4-iodo-phenothiazin-5-ium-3-methylamino-7-dimethylamino-chloride. The compositions are useful as lymphatic staining agents and/or, where at least a portion of the iodine is in the form of a radioactive iodine isotope, as radiolabeling agents for other lymphatic staining agents.

In another embodiment of the invention, there is provided a process for making a radiolabeled derivative of methylene blue. The process is carried out by contacting phenothiazin-5-ium-3,7-bis(dimethylamino)-chloride and I-125 in the presence of supported iodogen oxidizing agent to form a reaction product which has been iodinated with I-125.

Under preferred conditions, the reaction product made by this technique is known to be stable for a period of several weeks.

In a further embodiment of the invention, there is provided a method for making an injectable radiolabeled lymphatic staining agent available to a user. The method is carried out by selecting a lymphatic staining agent, radiolabeling the selected lymphatic staining agent to form a radiolabeled lymphatic staining agent, shipping the radiolabeled lymphatic staining agent to a hospital, and mixing the radiolabeled lymphatic staining agent at the hospital with a much larger amount, on a weight basis, of a non-radiolabeled lymphatic staining agent to form an injectable radiolabeled lymphatic staining agent suitable for surgical use in humans.

The method provides a more economical procedure for supplying radiolabeled lymphatic staining agent than current practice, in which the radioactive agent is made on site daily, or the entirety of the injectable staining agent is radiolabeled. In the preferred embodiment, the radioisotope selected has a half-life in the range of 2 days to 2 years, to avoid excessive loss of radioactivity during the shipment process.

DETAILED DESCRIPTION OF THE INVENTION

In one aspect, the present invention relates to iodinated methylene blue (methylene blue being phenothiazin-5-ium-3,7-bis(dimethylamino)-chloride, also known as methylthioninium chloride; tetramethylthionine chloride trihydrate; 3,9-bisdimethylaminophenazothionium chloride (1973 CRC); 3,7 bis(dimethylamino)phenazathionium chloride trihydrate; 3,7-bis(dimethylamino)phenothiazin-5-ium chloride; and phenothiazin-5-ium, 3,7-bis(dimethylamino)-chloride, trihydrate; Basic Blue 9, trihydrate; CAS #61-73-4).

In accordance with this embodiment of the invention, there is provided a composition of matter selected from the group consisting of phenothiazin-5-ium-3,7-bis(dimethylamino)-iodide; 4-iodo-phenothiazin-5-ium-3,7-bis(dimethylamino)-chloride; 4-iodo-phenothiazin-5-ium-3,7-bis(dimethylamino)-iodide; 4,6-diiodo-phenothiazin-5-ium-3,7-bis(dimethylamino)-chloride; 4,6-diiodo-phenothiazin-5-ium-3,7-bis(dimethylamino)-iodide; 4,6-diiodo-phenothiazin-5-ium-3,7-bis(methylamino)-chloride and 4-iodo-phenothiazin-5-ium-3-methylamino-7-dimethylamino-chloride.

The compositions which retain adequate coloration are usefully employed as lymphatic staining agents, for example to identify the sentinel node for a site in essentially the same manner as is known for methylene blue. Because of the intended use, it is acceptable for the compositions to contain a minor amount of unreacted phenothiazin-5-ium-3,7-bis(dimethylamino)-chloride.

Preferably, a substantial portion of the iodine in the compositions is selected from the group consisting of Iodine-125 isotope and Iodine-131 isotope. More preferably, a major portion of the iodine is in one of these radioactive isotopic forms. Most preferably, substantially all of the iodine is in one of these radioactive isotopic forms. In an exemplary embodiment, substantially all of the iodine is I-125 isotope. Iodine-125 isotope has a half-life of 60 days. This relatively long half life enables I-125 radiolabeled products to be commercially economically viable.

When injected in or near a breast tumor site, the preferred compositions will migrate along the lymphatic system to the sentinel node draining the site. Most preferably, the compositions are injected into a patient in the form of a near-neutral salt solution. The emissions from the I-125 enable remote tracing of the lymphatic ductwork to the sentinel node, and the sentinel node can be visually identified by the coloration imparted by the composition, in combination with other coloring agents where adequate coloration is not retained, as well as by emissions from the I-125.

For the sentinel node identification described above, it is not necessary that the totality of the dyestuff used be in radiolabeled form. It is much more cost effective to combine a small amount of the radiolabeled dyestuff with a much larger amount of the ordinarily used dyestuff, for example, lymphazurine blue, as this material has an extremely long shelf life, has already been demonstrated to be safe and effective for sentinel node identification and is widely used, and can be stored on site. In this manner, the desired degree of coloration can be imparted to the sentinel node with minimal radiation exposure to the patient. For example, admixing small quantities of the I-125 labeled methylene blue dye (0.1 to 0.5 cc, for example) in a much larger (4.5 to 4.9 cc, for example) quantity of unlabeled dye (lymphazurin blue, for example) should offer the surgeon all of the benefits of a two-stage procedure in a single stage and offer enhanced intraoperative sensitivity based on the low energy of the I-125 gamma emissions (37 KeV).

The radiolabeled compositions of the invention are made by contacting phenothiazin-5-ium-3,7-bis(dimethylamino)-chloride and I-125 in the presence of supported iodogen (1,3,4,6-tetrachloro-3A,6A-diphenylgylcolouril, CAS #51592-06-4, also known as Iodo Gen) oxidizing agent to form a reaction product which has been iodinated with I-125. Preferably, the iodogen is coated on the inside of the reaction vessel, such as by being solvated in chloroform which is then evaporated from the reaction vessel.

The contacting is further preferably conducted in the presence of iodide and iodate anions. Dissolved alkali metal iodide and alkali metal iodate is suitable. Sodium iodate and calcium iodide are preferred because they have been used with good results.

The contacting is further preferably conducted in the presence of acetate anions. Sodium acetate and acetic acid, preferably both, have been used with good results.

The contracting is further preferably conducted under acidic conditions. Acidic conditions are provided by the acetic acid when it is used. Other acids, such as HCl may also be used.

The contacting is further preferably conducted by adding an acidic oxidizing solution containing the I-125 and the iodide, iodate and acetate anions to a reaction vessel containing the supported iodogen oxidizing agent and the phenothiazin-5-ium-3,7-bis(dimethylamino)-chloride.

The contacting is further preferably conducted under elevated temperatures, for example, in the range 75 to 100 degrees C. Conducting the contacting for one hour at 100 degrees C. has been used with good results.

For finishing, the reaction product is flowed through a strong anion exchange column to remove unreacted I-125 and purified reaction product is collected from the column. Preferably, the column is preconditioned with sodium hydroxide, sterile water, hydrochloric acid, and sodium chloride prior to the finishing step. A column containing AG1-X8 resin, 200-400 mesh, from Bio-Rad, Hercules, Calif. has been used with good results. The resin is characterized as a strong anion exchange resin in hydroxide form based on a styrene divinylbenzene matrix.

In a further embodiment of the invention, there is provided a method for making an injectable radiolabeled lymphatic staining agent available to a user. The method is carried out by selecting a lymphatic staining agent, radiolabeling the selected lymphatic staining agent to form a radiolabeled lymphatic staining agent, shipping the radiolabeled lymphatic staining agent to a hospital, and mixing the radiolabeled lymphatic staining agent at the hospital with a much larger amount, on a weight basis, of a non-radiolabeled lymphatic staining agent to form an injectable radiolabeled lymphatic staining agent suitable for surgical use in humans.

Preferably, the selected lymphatic staining agent is radiolabeled with a radioisotope having a half-life in the range of from 2 days to 2 years. The following radioisotopes meet this criterion and have medicinal applications (half-life shown in parentheses): Chromium-51 (28 d), Cobalt-60 (10.5 mth), Cobalt-57 (272 d), Erbium-169 (9.4 d), Gallium-67 (78 h), Indium-111 (2.8 d), Iodine-131 (8 d), Iodine-125 (60 d), Iridium-192 (74 d), Iron-59 (46 d), Lutetium-177 (6.7 d), Molybdenum-99 (66 h) Palladium-103 (17 d), Phosphorus-32 (14 d), Rhenium-186 (3.8 d), Rubidium-82 (65 h), Selenium-75 (120 d), Strontium-89 (50 d), Strontium-92 (25 d), Thallium-201 (73 h), Xenon-133 (5 d), Ytterbium-169 (32 d), and Yttrium-90 (64 h). Preferably, the radioisotope is selected from the group consisting of Iodine-131, and Iodine-125. More preferably, the radioisotope is Iodine-125 because of its excellent balance of properties for lymphatic mapping.

The lymphatic staining agent most preferably is methylene blue because it has been tested with good results.

The much larger amount of a non-radiolabeled lymphatic staining agent is most preferably selected from the group consisting of isosulfan blue, (N-[4-[4-(diethylamino)phenyl] (2,5-disulfophenyl)methylene]-2,5-cyclohexadien-1-ylidene]-N-ethylethanaminium hydroxide, inner salt, sodium salt, CAS #68238-36-8), methylene blue, (phenothiazin-5-ium-3,7-bis(dimethylamino)-chloride), patent blue (N-[4[[4-(diethylamino)phenyl]-2,4-disulfophenyl)methylene]-2, 5cyclohexadien-1-ylidene]-N-ethylethanaminium sodium salt, also known as sulphan blue, anhydro-4,4'bis(diethylamino)-triphenylmethanol-2",4"-disulphonic acid monosodium salt, acid blue 1, patent blue VF, food blue 3, CAS #129-17-9), and patent blue V (calcium chelated dimer of (N-[4[[4-(diethylamino)phenyl]-2,4-disulfo-5hydroxyphenyl)methylene]-2,5cyclohexadien-1-ylidene]-N-ethylethanaminium sodium salt, also known as disulfine blue, anhydro-4,4'bis(diethylamino)-triphenylmethanol-5"hydroxy-2",4"-disulphonic acid monosodium salt, acid blue 3, patent blue violet, food blue 3, CAS #3536-49-0). Other non-radiolabeled lymphatic staining agents to which the radiolabeled agent can be added include acid yellow 42, Napthol blue black, Nitrazine yellow, chrysophenine, Direct yellow 27, Reactive blue 4, Evan's blue and Chicago sky blue. Any of the foregoing lymphatic staining agents can further be employed as the selected lymphatic staining agent if desired. However, it is preferred that the selected lymphatic staining agent have a lower affinity for lymphatic tissue than the lymphatic staining agent employed in the larger amount, because it can be desirable that the radiation dissipate faster than the color in the event that the detector is being swamped. Lymphatic affinity generally increases in the order of: no sulfonic acid groups, one sulfonic acid group, two sulfonic acid groups separated by one atom, and two sulfonic acid groups separated by 2-6 atoms in the chemical structure of the staining agent. Most preferably, the much larger amount of a non-radiolabeled lymphatic staining agent is isosulfan blue, for example 1% isosulfan blue such as from US Surgical Corp., Norwalk, Conn. under the trademark Lymphazurin™. The amount of radioactive dyestuff added is generally dictated by the radioactivity desired, generally being kept below 10 mCi, as well as beneath the level at which it might cause toxic effects.

EXAMPLE

Methylene Blue I-125
Radioiodination Procedure
1. Pre coat a 10 ml vial with 1.0 mg of Iodogen.
2. To the pre-coated Iodogen vial add 5.0 mg of Methylene Blue in 0.5 ml 3. Add a predetermined amount of NaI-125 (10-100 mCi) to a 12×75 mm plastic reaction tube.
4. Add 1.0 ml of Sodium Acetate (0.1M) and Acetic Acid (0.1M) pH=5.0 to the reaction tube.
5. Add 1.0 ml Sodium Iodate (4 mg/ml) to the plastic reaction tube.
6. Add 285 µg of Calcium Iodide to the plastic reaction tube.
7. Mix reaction tube and transfer contents into the sealed Iodogen vial that contains 5.0 mg of Methylene Blue.
8. Place Iodogen reaction vial on to a mixer/heat plate and heat and mix at 100° C. for 1.0 hour.
9. After incubation allow 10 minutes for vial cooling, and remove contents in a 10.0 ml syringe.
10. Add 1.0 ml of sodium acetate/acetic acid 0.1M
11. Using 10.0 ml syringe that contains the Methylene Blue withdraw the 1.0 ml of sodium acetate/acetic acid used to rinse the Iodogen vial.
12. Elute the entire amount contained in the syringe through a column containing AG 1-X8 Resin in hydroxide form, 100-200 mesh, conditioned with Sodium Hydroxide, SWFI (Sterile water for injection, Abbott) Hydrochloric Acid and Sodium Chloride. Attach a sterilization filter on the end of the column and elute into a sterile septumnated glass vial.
13. Measure the activity and volume collected.

While certain preferred embodiments of the invention have been described herein, the invention is not to be construed as being so limited, except to the extent that such limitations are found in the claims.

We claim:
1. A method
comprising
contacting phenothiazin-5-ium-3,7-bis(dimethylamino)-chloride and an I-125 radioactive iodine isotope in the presence of an iodogen oxidizing agent coated on a support to form a radiolabeled derivative of methylene blue which has been iodinated with the I-125 radioactive iodine isotope,
wherein the contacting is further conducted in the presence of iodide and iodate anions,
wherein the iodide and iodate anions are provided in the form of a solution of sodium iodide and calcium iodate.
2. A method as in claim 1 wherein the contacting is further conducted in the presence of acetate anions.
3. A method as in claim 1 wherein the contacting is further conducted under acidic conditions.
4. A method as in claim 1 wherein the contacting is further conducted at a temperature in the range of 75 to 100 degrees C.
5. A method as in claim 1 further comprising
flowing the radiolabeled derivative of methylene blue through an anion exchange column to remove unreacted I-125 and collecting purified radiolabeled derivative of methylene blue from the column.
6. A method as in claim 5 further comprising, prior to flowing the radiolabeled derivative of methylene blue through the anion exchange column, conditioning the column with sodium hydroxide, sterile water, hydrochloric acid, and sodium chloride.
7. A method as in claim 2 wherein the acetate anions are provided in the form of a solution of sodium acetate and acetic acid.
8. A method as in claim 3 wherein the acidic conditions are provided by acetic acid.

* * * * *